(12) United States Patent
Loebbert et al.

(10) Patent No.: US 9,034,572 B2
(45) Date of Patent: May 19, 2015

(54) CALIBRATABLE SENSOR UNIT FOR REACTION VESSELS

(71) Applicant: HAMILTON BONADUZ AG, Bonaduz (CH)

(72) Inventors: Andreas Loebbert, Chur (CH); Dirk Schoenfuss, Tamins (CH)

(73) Assignee: HAMILTON BONADUZ AG, Bonaduz (CH)

( * ) Notice: Subject to any disclaimer, the term of this patent is extended or adjusted under 35 U.S.C. 154(b) by 141 days.

(21) Appl. No.: 13/930,174

(22) Filed: Jun. 28, 2013

(65) Prior Publication Data

US 2013/0291618 A1 Nov. 7, 2013

Related U.S. Application Data

(62) Division of application No. 13/024,662, filed on Feb. 20, 2011, now Pat. No. 8,673,624.

(30) Foreign Application Priority Data

Feb. 10, 2010 (DE) .......................... 10 2010 001 779

(51) Int. Cl.
| | |
|---|---|
| *C12M 1/34* | (2006.01) |
| *C12M 3/00* | (2006.01) |
| *G01D 18/00* | (2006.01) |
| *G01N 33/00* | (2006.01) |
| *C12M 1/00* | (2006.01) |
| *G01N 27/416* | (2006.01) |

(Continued)

(52) U.S. Cl.
CPC .............. *G01N 33/00* (2013.01); *C12M 23/28* (2013.01); *C12M 41/26* (2013.01); *C12M 41/32* (2013.01); *C12M 41/34* (2013.01); *C12M 41/36* (2013.01); *C12M 41/40* (2013.01); *G01N 27/4165* (2013.01); *G01N 33/84* (2013.01); *G01N 27/283* (2013.01)

(58) Field of Classification Search
CPC ...... C12M 21/00; C12M 23/28; C12M 41/00; C12M 41/30
USPC .............. 435/4, 287.1, 287.2, 289.1; 73/1.01, 73/1.02, 1.03
See application file for complete search history.

(56) References Cited

U.S. PATENT DOCUMENTS

| | | | |
|---|---|---|---|
| 4,413,628 | A | 11/1983 | Tamulis |
| 5,284,570 | A | 2/1994 | Savage |

(Continued)

FOREIGN PATENT DOCUMENTS

| | | | |
|---|---|---|---|
| EP | 0354895 | A2 | 7/1989 |
| EP | 2 065 701 | A2 | 6/2009 |

(Continued)

*Primary Examiner* — Nathan Bowers
(74) *Attorney, Agent, or Firm* — Rothwell, Figg, Ernst & Manbeck, P.C.

(57) ABSTRACT

The present invention relates to a calibration method of a sensor unit connected to a reaction vessel, wherein the sensor unit comprises at least one sensor device configured to be calibrated, at least one compartment containing a calibrating agent, and a housing. The method comprising inserting a sensitive element of the at least one sensor device into a compartment of the sensor unit containing a calibrating agent, withdrawing the sensitive element from the compartment; inserting the sensitive element into the reaction vessel and locking the sensor device in position, wherein the steps of the method are irreversible.

6 Claims, 7 Drawing Sheets

(51) Int. Cl.
*G01N 33/84* (2006.01)
*G01N 27/28* (2006.01)

(56) References Cited

U.S. PATENT DOCUMENTS

| | | | |
|---|---|---|---|
| 5,514,339 A | 5/1996 | Leopardi et al. | |
| 5,939,610 A | 8/1999 | Iwamoto et al. | |
| 2001/0028865 A1 | 10/2001 | Cummings | |
| 2006/0258929 A1 | 11/2006 | Goode, Jr. | |
| 2010/0255526 A1 | 10/2010 | Braet et al. | |
| 2010/0291674 A1* | 11/2010 | Beese et al. | 435/325 |
| 2014/0349385 A1* | 11/2014 | Erdenberger et al. | 435/302.1 |

FOREIGN PATENT DOCUMENTS

| | | |
|---|---|---|
| WO | 2007048821 A2 | 5/2007 |
| WO | 2009059645 A1 | 5/2009 |

\* cited by examiner

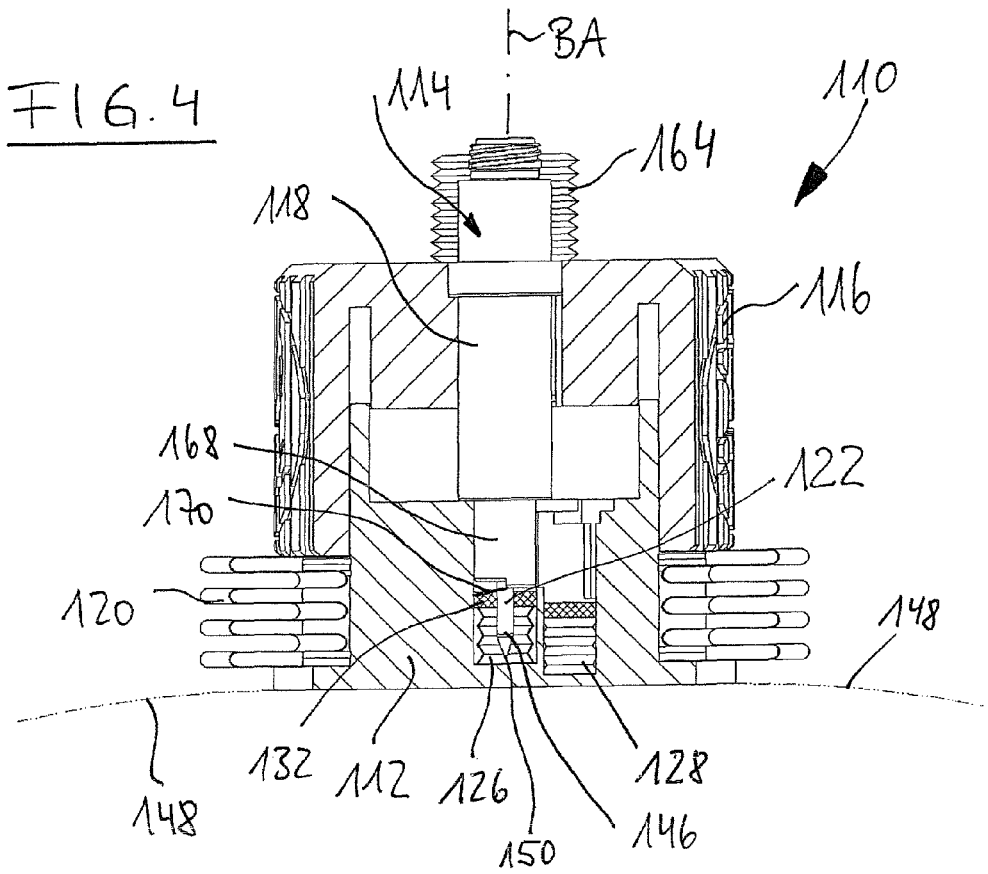
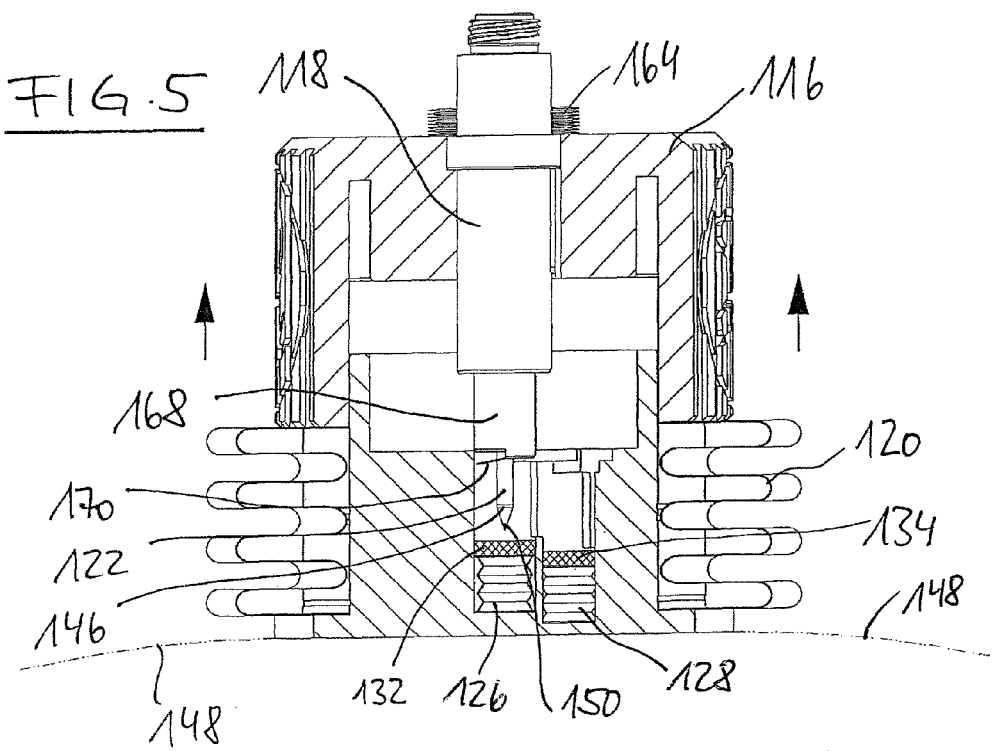

CALIBRATABLE SENSOR UNIT FOR REACTION VESSELS

This application is a divisional of U.S. Ser. No. 13/024,662 filed Feb. 10, 2011, now U.S. Pat. No. 8,673,624, which claims the benefit of German Patent Application No. 10 2010 001 779.5 filed on Feb. 10, 2010, the disclosures of which are incorporated herein in their entirety by reference.

DESCRIPTION

The present invention relates to a calibratable sensor unit for a reaction vessel, such as for example a fermenter, in particular a disposable (single-use) fermenter, comprising at least one sensor device to be calibrated and at least one compartment containing a calibrating agent, the at least one sensor device and the at least one compartment being accommodated movably relative to one another in a housing that is connected to or can be connected to the reaction vessel, wherein the sensor unit is arranged so as to calibrate the at least one sensor device by contact with the calibrating agent before chemical and/or physical parameters of a measurement substance are measured with the at least one sensor device.

Such a sensor unit is known for example from EP 0 372 121 B1. The sensor device illustrated there can be introduced in the axial direction of a housing-type sleeve accommodating it into a fermenter and can be withdrawn from the latter. The sensor device has at its end to be introduced into the fermenter a sensitive element as well as a type of cover, by means of which the sleeve can be hermetically sealed with respect to the interior of the fermenter when the sensor device is retracted. When the sensor device has been fully inserted into the sleeve and thus sealed with respect to the fermenter, a cleaning agent or a calibrating agent can be introduced into the sleeve by means of feed inlets mounted on the sleeve, so that the sensitive element of the sensor device can be rinsed without the cleaning agent or calibrating agent being able to pass into the fermenter. By arranging three sealing rings that are disposed at predetermined spacings relative to one another in the axial direction, a type of sluice function can be implemented in co-operation with various internal peripheral walls of different diameters. This sluice function allows that, depending on the relative position of the sensor device to the surrounding housing, the cleaning agent or calibrating agent can rinse different regions in the interior of the calibrating unit. The sensor proposed in EP 0 372 121 B1 is reusable and can be used multiple times. Furthermore it is also replaceably accommodated in the sleeve and/or housing of the calibrating unit.

From U.S. Pat. No. 5,939,610 a measuring device is further known with a sensor that can be ejected from a sleeve-type housing. The sensor is stored in calibrating fluid in a compartment. In order to be able to eject the sensor in the axial direction from the surrounding sleeve, the measuring device has to be rotated so that the end at which the sensor will exit is aligned substantially vertically upwards. This alignment of the measuring device is necessary since otherwise calibrating fluid would flow out of the compartment during the ejection procedure of the sensor. The sensor can be multiply actuated by means of a spring-detent mechanism, similar to an actuation device in a ballpoint pen. When the sensor or its sensitive element has been ejected sufficiently far from the housing that a measurement can be carried out, the opening through which the sensor has exited and which can be closed and sealed by a swivellable cover is closed by the co-operation of the outer circumference of the sensor device and the inner circumference of the opening edge, so that no calibrating agent can escape during the measurement procedure. On account of the possible multiple use and actuation of the sensor there is the danger with such a measuring device that impurities adhering to the sensitive element of the sensor can pass into the calibrating fluid. This is furthermore promoted by the fact that also when retracting the sensor into the compartment with calibrating fluid the measuring device has to be held in the vertically upwardly aligned position described above.

In biotechnology and especially also in the pharmaceutical industry the use of so-called disposable fermenters has increased. Known steel reactors are increasingly being replaced by disposable fermenters made of plastics material. An example of such a disposable fermenter system is disclosed inter alia in US 2005/0239199 A1. The use of disposable fermenters leads to large time and cost savings, since expensive and complicated cleaning steps such as clean in process (CIP) and sterilisation in process (SIP), which are a necessary measure in the case of steel reactors in order to sterilise the steel fermenter for the next culture, can be omitted. A further advantage of disposable fermenters compared to conventional steel reactors is the exclusion of the risk of cross-contamination, since disposable fermenters are sterilised before use.

In order to be able to measure chemical and physical parameters in the fermentation mixture when using disposable fermenters, such as for example pH value, conductivity, dissolved oxygen, cell density, optical density, pressure, carbon dioxide content and other substance concentrations, corresponding sensors, in particular physical, chemical, electrochemical and/or optical, must also be provided on disposable fermenters. A precondition for the use of sensors in disposable fermenters however is that these have to be introduced into the reaction space (interior) of a disposable fermenter without contaminating the latter during the introduction. In this connection ease of handling, low costs and the ability to calibrate the sensors as simply as possible but nevertheless accurately, are desirable.

Various systems have been proposed for introducing chemical sensors into the reaction space of disposable fermenters. For example optical patches, such as polymer membranes in which optically active substances are immobilised, are integrated in a wall of the disposable fermenter. The optically active substances immobilised in the patches change their fluorescence signals for example depending on the partial pressure of the dissolved oxygen or the pH-value of the fermentation mixture, which can be measured and evaluated with corresponding excitation and detection devices mounted externally on the disposable fermenter. An example of such optical systems is disclosed in DE 101 37 530 A1 or US 2008/0032389 A1. A problem in the use of such patches is, apart from the limited choice of sensors, the low stability, for example in the case of pH-sensitive patches, of the employed optically active substances to γ-rays, which are used in the sterilisation. Since less "hard" irradiation with UVC- and β-rays is often too weak on account of their low penetration depth of only a few tenths of a millimeter, disposable fermenters are normally irradiated with γ-rays at circa 50 kGrey for sterilisation purposes. Furthermore, with such patches there is the danger that their optically active substances, which are generally toxic and carcinogenic, are released into the fermenter and as a result the contents are contaminated. Further problems arise due to the uncertainty concerning the long-term stability of the patches on account of ageing and the associated questionable quality of the preliminary calibration, so that in practice the external measurement of a sample taken from the disposable fermenter and a subsequent adjustment of the sensor system are as a rule necessary.

On account of their higher accuracy, sensory versatility, their larger measurement range and their greater robustness, it is desirable that also traditional sensors, such as for example the pH single-rod measuring chain, can be used also in disposable fermenters. Systems in which the sensor is integrated in the reactor, so that both can be sterilised together, represent one possibility of using traditional sensors in disposable fermenters. In this connection reference is made for example to WO 2009/059645 A1. The device proposed there permits in addition an end-point calibration, by integrating a pH sensor in a vessel together with a γ-sterilisable and pH-stable storage solution, which also serves as calibrating solution for an end-point calibration and is combined with the disposable fermenter. However, an end-point calibration is not sufficient for an accurate pH measurement with commercial pH sensors. Deviations of up to 0.25 pH units can occur. Since the storage solution and calibrating solution in the proposed system likewise reach the reaction space (interior of the fermenter) when the sensor is introduced, this can lead to a contamination of the fermentation mixture, especially with small fermenter volumes.

The object of the invention is to provide a calibratable sensor unit that enables a sensor to be calibrated accurately and reliably under sterile conditions and in a simple way. In this connection the sensory principle of the sensor that is used is not important.

In order to achieve this object it is proposed that a generic sensor unit is modified in such a way that the relative movement between the at least one sensor device and the at least one compartment can be carried out irreversibly, the at least one sensor device being movable relative to the at least one compartment from an initial position, in which the sensor device when correctly used cannot be contacted by the measurement substance, under a change of the surroundings of at least a part of the sensor device, in particular of a sensitive element, to a measurement readiness position different from the initial position, in which readiness position the sensor device can be contacted at least partially, in particular with a sensitive element, by the measurement substance.

Since the movement of the sensor device, in particular its sensitive element, cannot be reversed from the initial position back to the measurement readiness position, the sensitive element of the sensor device can be moved relative to the at least one compartment by means of an unambiguous and defined procedure. In this way a simple and error-free handling and manipulation can be ensured.

A reaction vessel is understood to mean any vessel in which a measurement substance is subjected to changes on account of chemical and/or biological reactions and/or on account of ageing. In this connection the changes can be monitored by sensors and if necessary interventions can be carried out in the reaction taking place in the reaction vessel.

By means of a preferred automatic holding of the sensor device in the measurement readiness position it is ensured that the sensitive element once it has been introduced into a reaction space of the reaction vessel (fermenter interior) remains there and can no longer be retracted into the housing of the calibrating unit. The danger of impurities and contamination is thereby reduced to a minimum or even prevented. Preferably the sensor device can be locked, in particular in an irreversible manner, in the measurement readiness position.

The housing of the sensor unit preferably surrounds the at least one sensor device in the initial position and the at least one compartment. In this way the sensor device and the compartments can be protected against external contamination.

In the initial position the sensor device, in particular its sensitive element, can be accommodated in an associated compartment with calibrating agent. This ensures that the sensitive element can be stored in a chemically favourable environment before it is actually used in the fermenter interior.

In order to be able to seal the at least one compartment, it can be closed by at least one septum. In this connection the compartment can be separated by means of the septum in particular from the interior of the sensor unit surrounded by the housing or from an adjacent compartment or from the fermenter. Preferably the at least one septum is prepared so that it can easily be penetrated or punctured by means of the sensor device. In particular the septum can comprise regions of different material thickness and/or can be perforated at least in part. In this case a perforation can completely penetrate the septum material or can however be implemented as a partial perforation, i.e. with at least one opening that does not extend over the whole material thickness of the septum. In order to be able to introduce the sensitive element of the at least one sensor device into the at least one compartment, it is proposed in this connection that the sensor device has a free end which is designed in such a way that the at least one septum of the at least one compartment can be penetrated, preferably in a direction substantially orthogonal to the plane of the septum.

The at least one compartment containing a calibrating agent can be designed as a unit closed on one or both sides by septa. The at least one septum can be joined by known techniques, such as for example bonding, welding, screwing or gluing, to walls of the at least one compartment.

The at least one septum is preferably configured so that the calibrating agent contained in the at least one compartment is permanently enclosed, but permits the passage of the sensory element. Furthermore it is particularly advantageous if the at least one septum is implemented in such a way that the sensor unit and/or the sensitive element on penetrating the at least one septum is at the same time cleansed of the calibrating agent. To this end it is proposed that the at least one septum can consist for example of single-layer or multilayer films or sheets of elastic polymers. Examples of possible polymers are PE, EVA and polyamides. The polymers that are used should be stable to ageing, chemicals and radiation, and should preferably also be FDA-compliant. As an alternative to the aforementioned polymers composite materials, polymer blends or elastomers, such as for example a (FDA-approved) microcellular rubber film, can also be used, which can be prepared beforehand for easier penetration, for example by providing regions of different material thickness, a (partial) perforation or the like. In this way a type of predetermined rupture point can be provided in a relevant septum.

The sensor unit can comprise several compartments, which are arranged behind one another in relation to the penetration direction of the sensor device and which are separated from one another by respective septa arranged therebetween. This enables for example several compartments to be arranged behind one another in the direction in which the sensor device is moved from the initial position to the end position introduced in the fermenter. Since the individual compartments are separated from one another by septa, this ensures that the calibrating agents contained in the compartments cannot intermix. In addition the stripping of calibrating agents of one compartment by the septa can be ensured before the sensitive element is introduced into the neighbouring compartment with another calibrating agent.

Alternatively or in addition the sensor unit can comprise several compartments, which are arranged relative to one another substantially orthogonal to the penetration direction. With such an arrangement of compartments the sensor device can be withdrawn from a first compartment and then after a feed motion to a next compartment can be introduced into this.

So long as a plurality of compartments are provided in a sensor unit, a cleaning agent can be contained in at least one of these compartments, by means of which the sensitive element of the sensor device can be cleaned to remove adhering impurities in order thereby to ensure that no measurement value errors caused by impurities, or possibly contamination in the reaction vessel, such as the fermenter, can occur.

In order to suppress the adherence of impurities still further, it is proposed to allocate a stripping device to the at least one compartment, which device can be penetrated by the sensor device and is designed in such a way that impurities adhering to the sensor device, in particular adhering calibrating agent or possibly cleaning agent, are retained in the relevant compartment with calibrating agent or possibly cleaning agent. As already mentioned above, the stripping device can be formed by at least one septum or by at least one additional stripping means adjacent to the septum in the penetration direction, in particular a sealing ring.

Preferably the calibrating unit comprises actuating means acting on the at least one sensor device, which are implemented in such a way that by means of the actuating means the irreversible relative movement between the at least one sensor device and the at least one compartment can be effected. As actuating means there may be used structural parts that can be manipulated from outside the housing, and which can be joined by widely differing types of mechanical connections to the sensor device and to the housing, so that as a result of the co-operation of the mechanical connections an irreversible guidance of the sensor device by means of the actuating means takes place. Such mechanical connections may for example be threads, spring-groove engagements, locking means or the like.

The calibrating agent and/or the cleaning agent is preferably formulated as a sterilisable viscous medium, in particular as a gel or paste. Such calibrating agents, in particular highly viscous agents, are dimensionally stable and, in contrast to liquids, do not run. This can be particularly advantageous if a compartment also contains a gaseous phase. A gaseous phase present on the sensitive element can interfere with or even completely invalidate the calibration. A compressible gaseous phase in a compartment is necessary however in order to compensate the displacement of calibrating agent through the sensor dipping into the compartment, so long as the relevant compartment is provided with rigid walls. In such a case it is preferred that the ratio of gel phase to gaseous phase is chosen so that the sensor remains sufficiently wetted with calibrating agent in every position. In this way it is possible to use the sensor unit in any arbitrary alignment of the sensor device.

If less viscous, more flowable calibrating agents or cleaning agents are to be used, it is conceivable to avoid a gaseous phase in the at least one compartment. In order to be able to compensate the increase in volume resulting from the insertion of the sensor device into the at least one compartment, the at least one compartment can have flexible walls, for example in the form of a type of bellows.

The at least one calibrating agent can contain a synthetic polymer, in particular polyvinyl alcohol or hydroxyethylcellulose, or natural polymers, in particular polysaccharides, as thickening agent.

According to a further aspect the invention also relates to a reaction vessel, such as a fermenter, in particular a disposable fermenter, with a reaction space and a calibrating unit, which is rigidly connected, in particular screwed, bonded or welded, thereto with at least one of the features mentioned above, wherein the reaction vessel and the calibratable sensor unit are sterilisable or sterilised together.

By way of development it is proposed that in a reaction vessel the sensor device in the already discussed measurement readiness position is at least partly accommodated, in particular with its sensitive element, in the reaction space.

The reaction space can be separated from the sensor unit by at least one septum associated with the reaction vessel and/or with the sensor unit. This allows on the one hand a seal to be created between the reaction space and sensor unit, and on the other hand provides an access for the sensor device into the reaction space on penetration of the septum.

Furthermore a method is also proposed for calibrating at least one sensor device of a sensor unit with at least one of the features mentioned above connected to a reaction vessel, such as a fermenter, in particular a disposable fermenter, this method comprising the following steps:
  a) Insertion of a sensitive element of the at least one sensor device into a compartment of the sensor unit containing a calibrating agent,
  b) withdrawal of the sensitive element from the compartment,
  c) insertion of the sensitive element into the reaction vessel and locking the sensor device in position,
    wherein the steps a) to c) are carried out irreversibly.

By way of development of the method, it is proposed that the steps a) and b) be carried out on at least one further compartment containing a further calibrating agent or a cleaning agent, before executing the step c).

On repeating the steps a) and b) on each further compartment, the at least one sensor device is guided, if necessary temporarily stopped, so that the sensitive element no longer comes into contact with a preceding compartment.

The invention is described hereinafter by way of example and in a non-limiting manner with reference to the accompanying figures on the basis of two embodiments. In the drawings:

FIGS. 4 to 10 show sectional views of the sensor unit of FIG. 3 in various positions during its use.

The invention is described in more detail hereinafter with the aid of two embodiments, so-called pH single-rod measuring chains being described purely by way of example as sensors. This in no way limits the sensor unit to such sensors, and other sensors can equally well be provided for measuring further chemical and/or physical properties. Furthermore it is also pointed out that the number of sensors illustrated in the examples of implementation, which are described with the respective sensor unit, should likewise not be regarded as limiting, but that in addition to the illustrated sensor units with one or two sensors, more sensors may also be provided in a sensor unit. It is moreover pointed out that not just one of the following embodiments of the sensor unit can be arranged on a reaction vessel, such as a fermenter, in particular a disposable fermenter, but that also a plurality of such sensor units, possibly also different types of sensor units, can be installed at different sites of a reaction vessel. A fermenter is described hereinafter as reaction vessel, but should in no way be understood as limiting.

Figure 1:
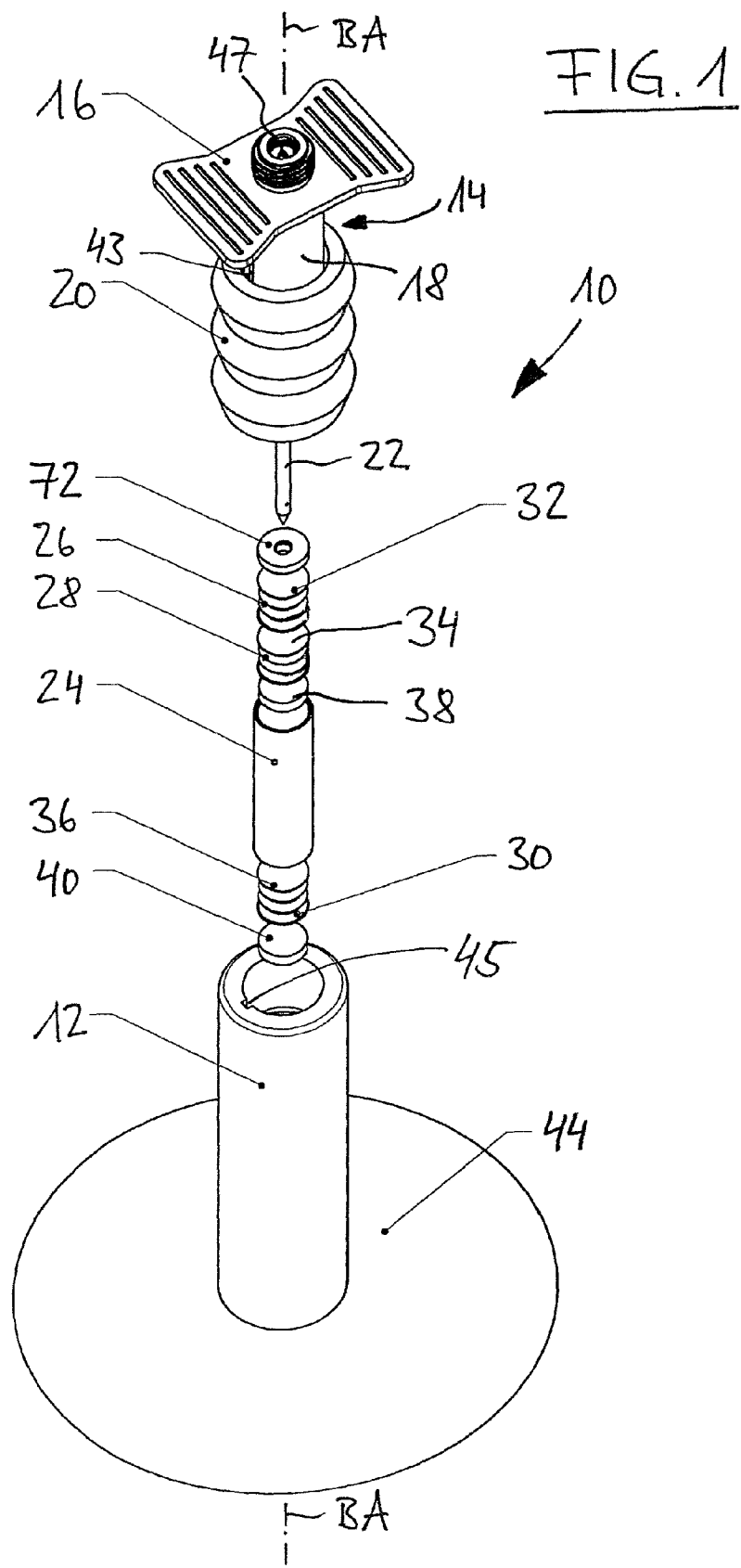
FIG. 1 shows in a schematic and perspective exploded view a calibratable sensor unit according to a first embodiment of the invention.

A first embodiment of a sensor unit 10 schematically illustrated in FIG. 1 comprises a sleeve-like or connector-like housing 12, which in its longitudinal direction defines a movement axis BA along which a sensor device 14 can be moved. The sensor device 14 comprises at its upper end a plate-like or wing-like actuating element 16, which is arranged outside the housing 12 and can be gripped by a user. The actuating element 16 is joined to a guide sleeve 18, which can extend in the direction BA substantially orthogonal to the actuating element 16. In order to seal the housing 12 a sealing element 20, for example in this case bellows 20, can be arranged around the guide sleeve, so as to seal the interior of the housing 12 against the surroundings. A sensor 22 is connected to the guide sleeve 18 and to the actuating element 16. This sensor 22 is, as already mentioned in the introduction to the description of the figures, implemented as a pH one-rod measuring chain. A receiving sleeve 24 is arranged in the housing 12, and is provided so as to receive a plurality of compartments, in the present example three compartments 26, 28 and 30. The compartments 26, 28 and 30 are separated and sealed from one another by means of septa 32, 34 and 36. So-called cleaning septa 38 and 40 are arranged between the compartments 28 and 30 as well as in the direction BA downwards adjoining the compartment 30, which serve to retain impurities adhering to the sensor 22 during penetration through the relevant septum 38, 40, so that no impurities reach the next compartment (here the compartment 30) or subsequently the fermenter (not shown), adjoining the calibrating unit 10 in the direction BA downwards.

The receiving sleeve 24, the housing 12 and the guide sleeve 18 are dimensioned so that the sensor device 14 can be moved relative to the receiving sleeve 24 and to the compartments 26, 28, 30 accommodated therein in the direction BA from the top downwards, referred to the chosen illustration. In the movement of the sensor device 14 relative to the receiving sleeve 24 and to the housing 12 the guide sleeve 18 is accommodated in the radial direction between the receiving sleeve 24 and the housing 12. On the guide sleeve 18 in the lower end regions there are provided in particular spring-urged stop projections 42 (FIG. 2a), which can engage in corresponding stop recesses that can be provided on an inner circumferential wall of the housing 12. In order to prevent a rotation of the guide sleeve 18 about the axis BA the sleeve engages via a projection denoted by the reference numeral 43 with a guide groove 45 formed in the housing 12. Furthermore it is also pointed out that the sensor device 14 has at its upper end (facing away from the fermenter) a connection piece 47, to which the sensor can be connected with a measuring device or the like.

At its end associated with a fermenter (not shown; FIG. 1, lower end referred to the direction BA), the sensor unit 10 has a plate-like fastening element 44, by means of which the sensor unit 10 can be connected to a fermenter. Preferably the fastening element 44 is formed as a type of welded-on lip, which can be bonded or welded to the fermenter. In this connection it is particularly preferred if the welded-on lip 44 as well as the fermenter are made of a plastics material, which may be the case in particular with so-called disposable fermenters. A screw connection or some other type of releasable connection between the sensor unit and fermenter is also conceivable.

Figure 2:
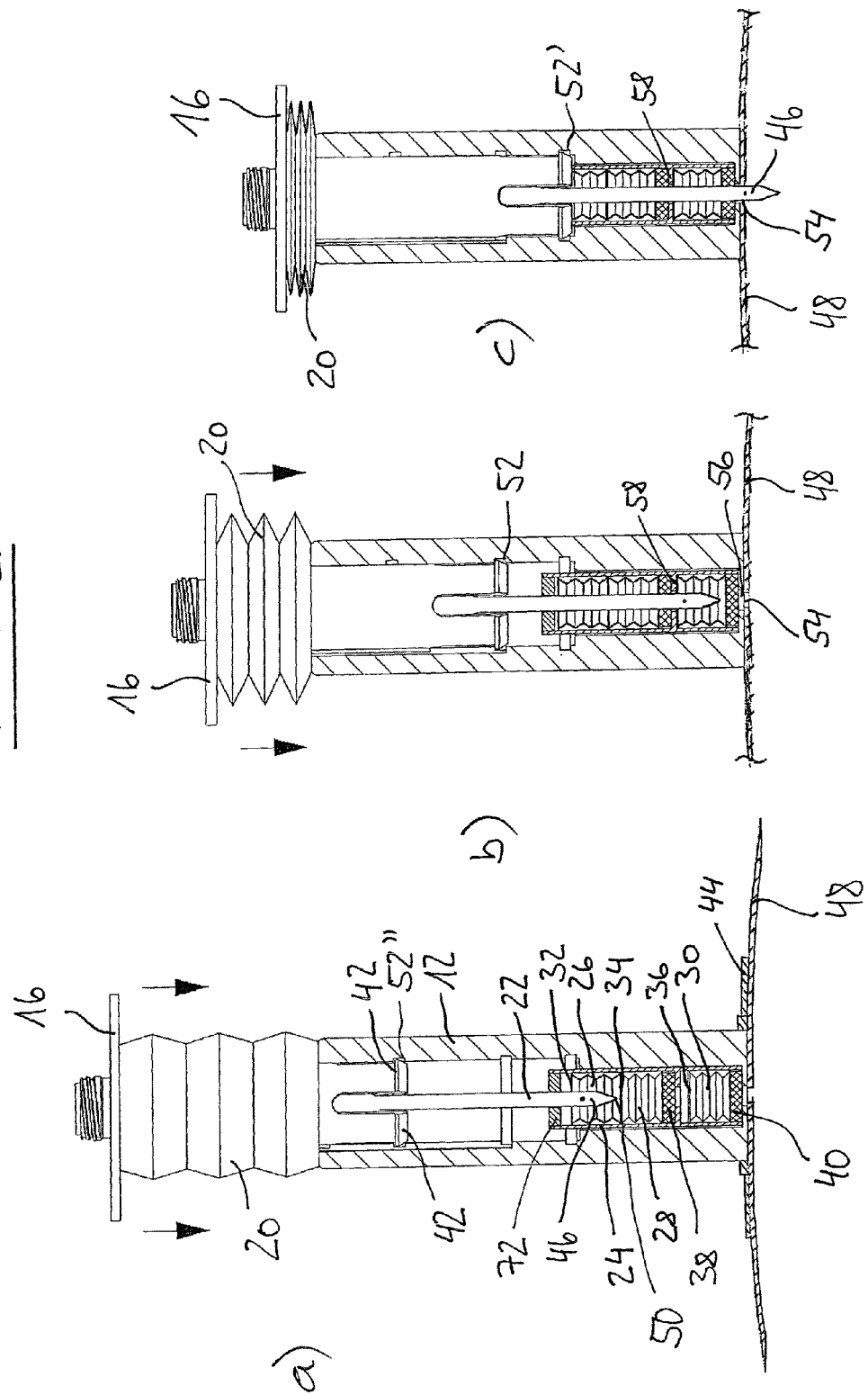
FIG. 2 shows in the part-figures a) to c) the sensor unit of FIG. 1 in a longitudinal sectional view in various positions during its use.

FIG. 2 shows in the part figures a) to c) the movement on the sensor 22 from an initial position (FIG. 2a) via an intermediate position (FIG. 2b) to a measurement readiness position (FIG. 2c), in which the sensor 22 is arranged with its lower or front sensitive region or sensitive element 46 in an interior (reaction space) of a fermenter 48 (reaction vessel) indicated only implicitly here.

In the initial position according to FIG. 2a) the sensor 22 together with its sensitive element 46 is located in the compartment 26, which is filled with a calibrating agent, for example a pH buffer gel of pH 4. In this initial position a calibration of the sensor 22 can be carried out on the basis of the buffer gel accommodated in the compartment 26. After carrying out this first calibration step the sensor 22 is moved by means of the actuating element 16 in the direction of the fermenter 48. At the same time the sensor 22 together with its end 50, which can be implemented as a sharp tip, facing towards the fermenter 48 penetrates the septum 34 separating and sealing the compartment 26 from the compartment 28. The compartment 28 may contain a cleaning agent, so that the sensor 22, in particular its sensitive end 46, can be cleansed of impurities with calibrating agent from the compartment 26. On further movement of the actuating element 16 and sensor 22 together with the guide sleeve 18 towards the fermenter 48, the tip 50 penetrates the cleaning septum 38 as well as the septum 36 sealing the compartment 30, so that the sensitive element 46 is now located according to FIG. 2b) in the compartment 30. In this position the stop projections 42 of the guide sleeve 18 engage in a locking manner with stop recesses 52 provided in the housing 12. The stop recesses can also be designed in the form of a type of annular groove as a single stop recess 52. The stop projections 42 are preferably designed in such a way that they engage with the stop recesses 52 so that a movement of the actuating element 16 and thus of the sensor 22 away from the fermenter 48 is impossible or can be executed only by exerting a strong force. In this way the co-operation of stop projections 42 and stop recesses 52 constitutes a type of locking of the sensor device 14 relative to the compartments 26, 28, 30. Since the stop projections 42 towards the fermenter preferably have a conically shaped circumferential surface, they can be guided inwardly from the stop recess 52 in the direction of the fermenter 48 under elastic radial deflection.

The compartment 30 can contain a further calibrating agent, for example a pH 7 buffer gel, so that a further calibration of the sensor 22 can be carried out in the intermediate position illustrated in FIG. 2b).

After this second calibration has been carried out the actuating element 16 can be moved further in the direction of the fermenter 48, so that the sensor 22, in particular its sensitive element 46, can be moved straight through the cleaning septum 40 and through an opening 54 provided in the fermenter 48, into the interior of the fermenter 48. In this connection it is pointed out that also the housing 12 can have an opening 56 adjacent to the opening 54 of the fermenter 48, provided for the passage of the sensor 22. This can likewise be closed by a septum.

As illustrated in FIG. 2c), the stop projections 42 of the guide sleeve 18 likewise engage in the illustrated end position of the sensor 22 in one or more stop recesses 52', so that the actuating element 16 and thus the sensor 22 cannot be moved in the direction away from the fermenter 48.

It is pointed out that in the illustrated embodiment the compartments 26, 28 and 30 are formed as bellows and are completely filled with the respective calibrating agent or cleaning agent, without the presence of any gaseous phase in the relevant compartment. On penetration of the sensor 22 into the compartments these expand within the receiving sleeve 24 on account of the displacement of the calibrating or cleaning agent in the longitudinal direction. It is furthermore pointed out that the receiving sleeve 24 may have a radially inwardly pointing projection 58, on which the cleaning septum 38 is supported. The compartment 30 is thus accommodated between this projection 58 and the lower edge of the housing 12 forming the opening 56.

The movement of the sensor 22 and of its sensitive element 46 from the initial position according to FIG. 2a) to the end position according to FIG. 2c) takes place irreversibly, so that the sensitive element 46 can be moved in a well-defined manner from the first compartment 26 into the second compartment 28, the third compartment 30 and finally into the interior of the fermenter 48. A movement of the sensor 22 away from the fermenter 48 is prevented by the engagement between the stop projections 42 of the guide sleeve 18 and the stop recesses 52 and 52' in the housing 12. It should also be noted in this connection that the stop projections 42 can also be accommodated in the initial position according to FIG. 2a) in a stop recess 52", so that the sensor 22 and the sensitive element 46 are securely held in this initial position and the sensitive element 46 is accommodated in the buffer solution of the compartment 26.

Figure 3:
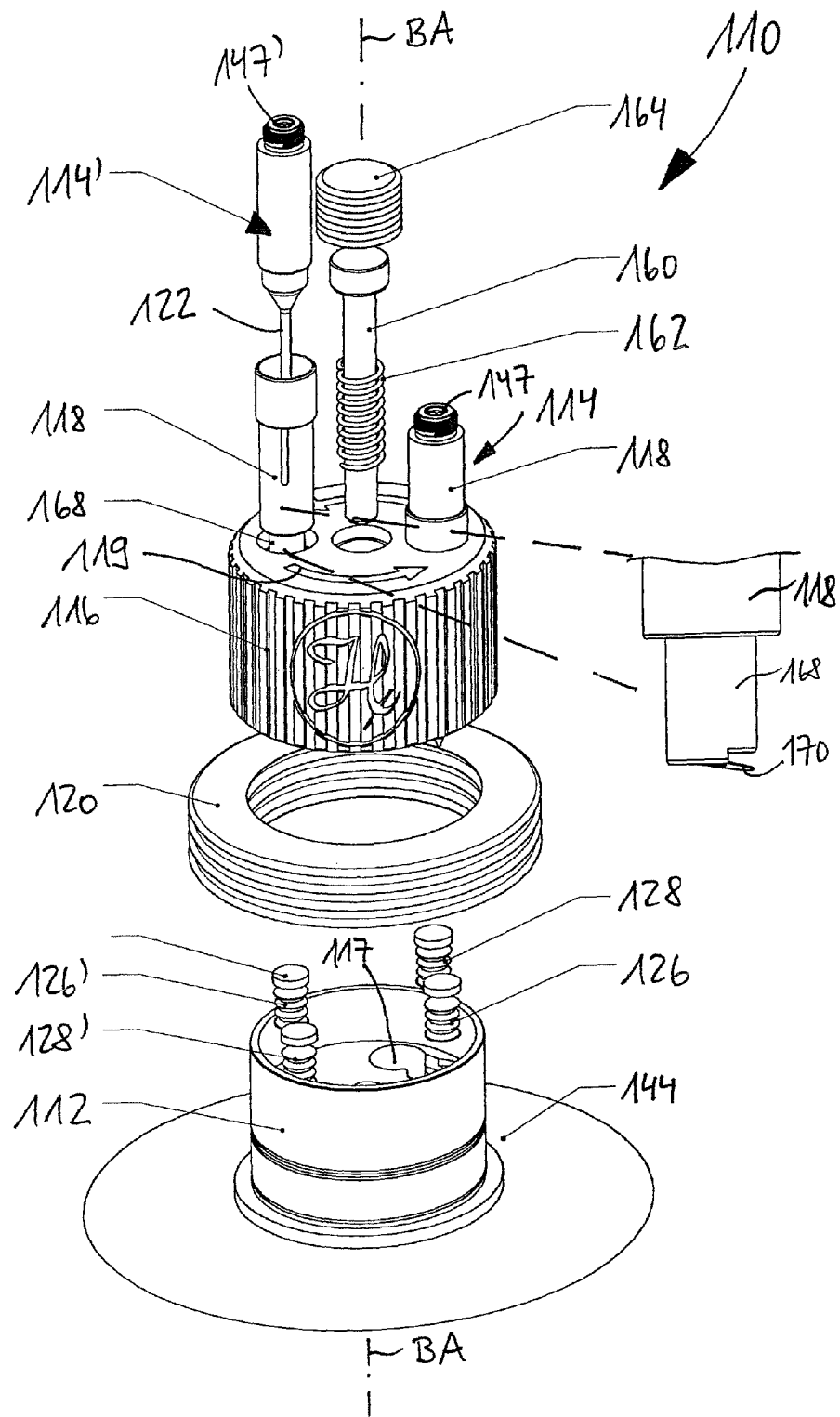
FIG. 3 shows a schematic and perspective exploded view of a second embodiment of the sensor unit according to the invention.

FIG. 3 shows a second embodiment of a sensor unit, in which structural parts that are similar or identical to the first embodiment are denoted by the same reference numerals increased by 100.

Figure 11:
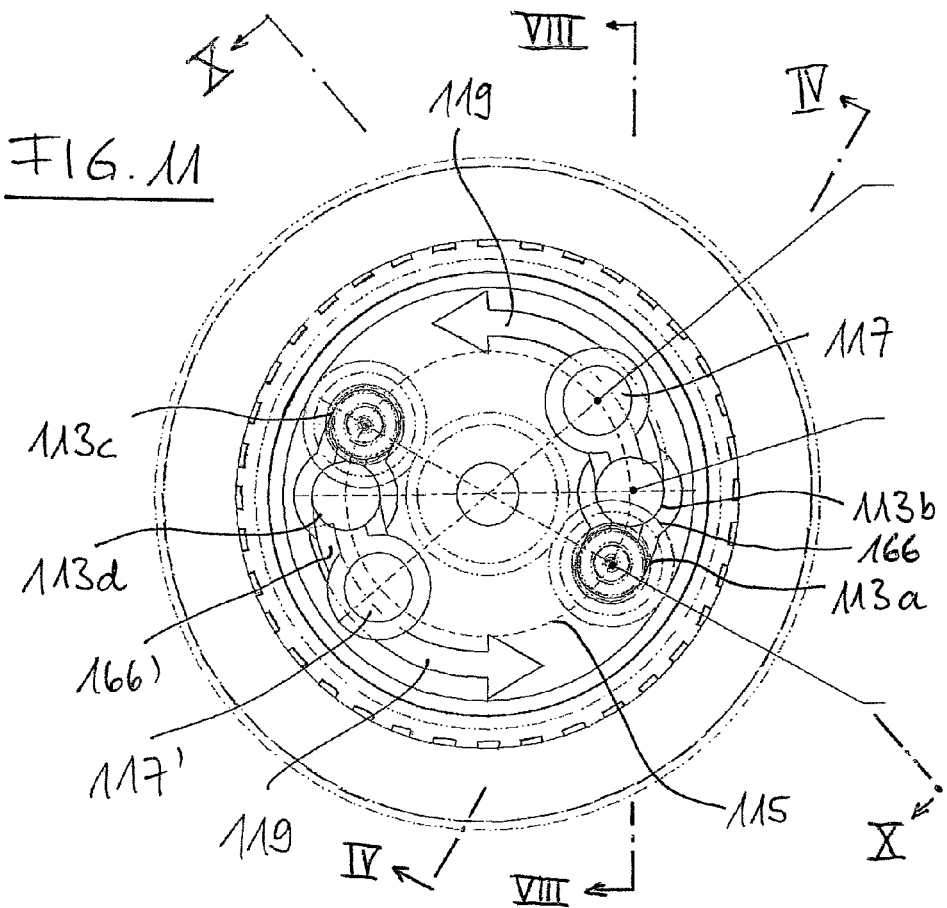
FIG. 11 shows a schematic plan view of the sensor unit of FIG. 3.

A sensor unit 110 according to a second embodiment comprises a housing 112, which is preferably implemented in the form of a connector or tube, receptacles being provided in the interior of the housing in which compartments 126, 126', 128 and 128' can be accommodated. The receptacles can clearly be seen for example in FIG. 11 and are provided with the reference numerals 113a to 113d. As can be seen on comparing FIG. 3 and FIG. 11, the compartments 126, 126', 128 and 128' are arranged next to one another along a curved, preferably circular, line 115. In this connection the compartments 126, 128 and 126', 128' form respective groups of compartments for a respective sensor device 114, 114' (FIG. 3). Connecting passages 117 and 117' are also provided adjacent to the receptacles 113b and 113d in the housing 12, through which the respective sensor device 114, 114' can be moved into an associated fermenter.

The sensor devices 114, 114' are accommodated in an actuating element 116 and are preferably firmly connected to the latter. The actuating element 116 is preferably designed as a type of cap, which can be turned relative to the housing 112 in the direction of the arrow 119 (here for example anti-clockwise). The rotation takes place about an axis or shaft 160 connected to the housing 112. The actuating element 116 can be moved up and down, i.e. away from the fermenter and towards the fermenter, along the axial direction BA of the shaft 160. Preferably the actuating element 116 is pretensioned in the direction of the fermenter by means of a spring 162.

A seal is effected between the actuating element 116 and the housing 112 by means of bellows 120, and a further seal is effected between the stationery shaft 160 and the actuating element 116 by means of further bellows 164. In this embodiment too pH single-rod measuring chains 122 for example can be used as sensors. As can be seen from FIG. 3, two sensor devices 114, 114' are provided in the actuating element 116, which can be caused to move jointly by means of the actuating element 116. It is pointed out that the sensor devices 114, 114' can also be different sensors, for example a pH sensor and a sensor for measuring the oxygen content or the like.

The rotation of the actuating element 116 in the direction of the arrow 119 (here anti-clockwise) is preferably only allowed if the actuating element 116 is moved upwardly against the pretensioning exerted by the spring 162. In addition the recesses 113a to 113d, the connecting passages 117, 117' are joined to one another by grooves or guides 166 and 166', so that in co-operation with the respective sleeves 118 (or sleeve 118' not visible) surrounding the sensors 122, a rotation of the actuating element 116 in the opposite direction (here clockwise) is prevented. Through the rotational movement and the raising and lowering of the actuating element 116 the sensor devices 114, 114' can be brought to the respective associated compartments 126, 128 and 126', 128'. Furthermore, in a last step the feed of the sensor device 114, 114' to the fermenter can take place through the connecting passages 117, 117'.

It should be noted that a welded-on lip 144 is provided on the housing 112, by means of which the sensor unit 110 can be joined to an associated fermenter, preferably a disposable fermenter. In addition the sensor devices 114, 114' have respective connecting pieces 147, 147' for connection to a measuring device or the like.

The guide sleeve 118 receiving the sensor 122 has in its lower section a type of journal 168, which is guided by the edges and grooves 166, 166'. The journal 168 has an elastic locking element 170 pretensioned downwardly and towards the fermenter, which by co-operating with guides and grooves 166, 166' formed in the housing 112 and with circumferential edges of the receptacles 113a to 113d, can prevent a rotation of the actuating element 116 in the opposite direction to the arrow 119.

The movement sequence and the calibration procedure are described hereinafter with reference to FIGS. 4 to 10 by the example of the sensor device 114. Here FIGS. 4 to 10 illustrate sections running tangentially to the arc 115, as is shown by way of example by the sectional lines IV-IV, VIII-VIII and X-X in FIG. 11. The steps illustrated in FIGS. 5 to 7 and 9 are likewise tangential sections at intermediate positions, and for the sake of comprehension corresponding further sectional lines have been omitted in FIG. 11.

Figure 6:
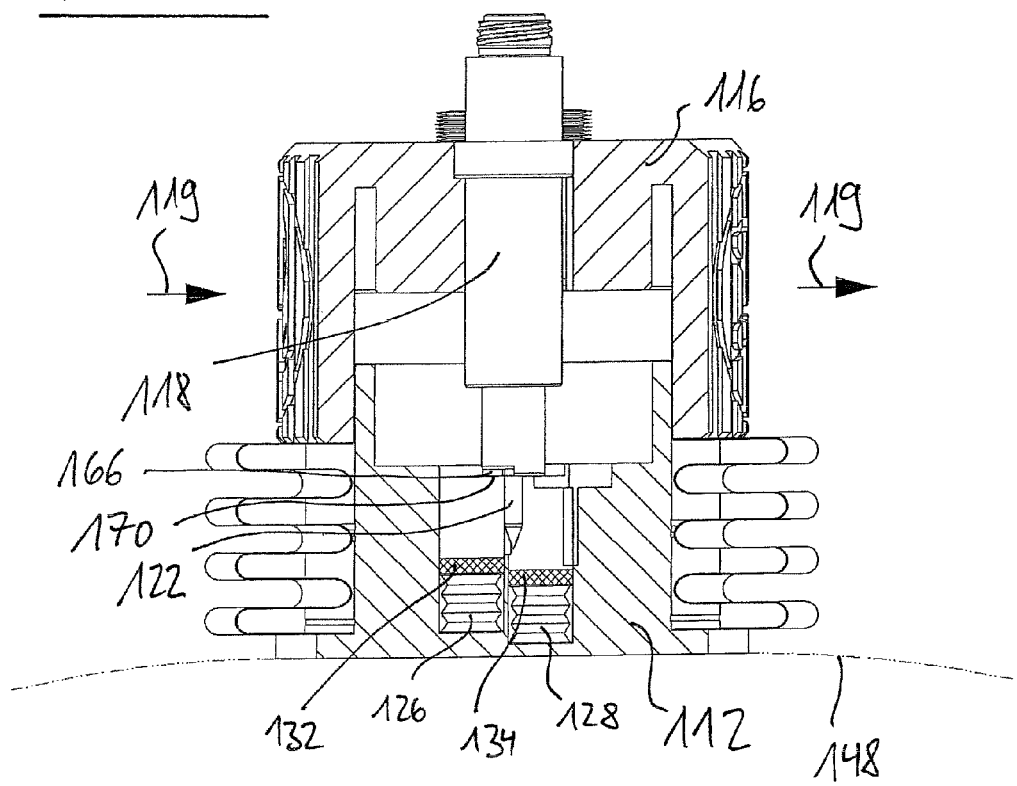
Figure 7:
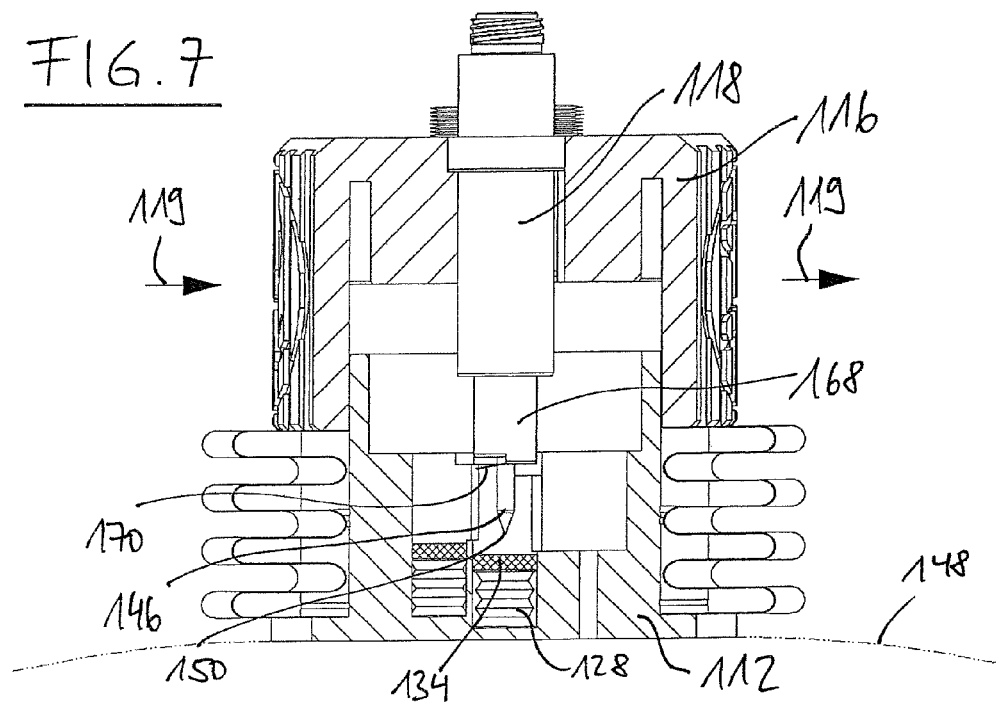

FIG. 4 shows the assembled sensor unit 110 in a so-called initial position. In this initial position the sensor 122, in particular its sensitive element 146, is accommodated in the compartment 126. This compartment 126 can contain a calibrating agent, for example a pH buffer solution. The compartment 126 is closed to the inside of the housing 112 and sensor unit 110 by means of a septum 132 that can penetrate through the sensor 122. The septum 132 can also have a cleaning action, so that when the sensor 122 is withdrawn from the compartment 126 impurities adhering to the sensor can mostly be retained in the compartment 126. As can further be seen from the figure, the actuating element in this initial position illustrated here cannot be rotated clockwise about the axis BA, since the locking element 170 provided on the sleeve 118 and on the journal 168 bears against an edge of the housing 112 preventing this rotation In order to bring the sensor 122 into operation for measurements in the fermenter 148, after carrying out a first calibration in the compartment 126 the actuating element 116 can be moved upwards along the axis or shaft 160 (FIG. 3), in other words away from the fermenter 148, so that the guide sleeve 118 and the sensor 122 are moved upwardly together with it. After the actuating element 116 has been moved upwards by a certain distance, a rotational movement about the axis and shaft 160 (FIG. 3) in the direction of the arrow 119 (counter-clockwise) can take place, as is illustrated in FIG. 6, whereby the sensor 122 can be moved from the receptacle 113a to the receptacle 113b (FIG. 11) along the movement line 115. In this rotational movement the locking element 170 is in a roughly horizontal arrangement on a guide edge or a groove 166, which is formed between the two receptacles 113a, 113b, as can be seen in FIG. 6. As soon as the sensor 122 is roughly in alignment with the receptacle 113b (FIG. 7) the locking element 170 is moved on account of its elastic pretensioning into the receptacle 113b and engages behind its inner edge, so that a rotational movement against the direction of the arrow 119 shown in FIGS. 6 and 7 is no longer possible. After completion of the rotational movement from the first receptacle 113a to the second receptacle 113b, a lowering of the actuating element 116 takes place in the direction of the fermenter 148, so that the sensor 122, in particular its sensitive element 146, can be moved into the compartment 128. In this feed motion of the actuating element 118 along the axis and shaft 160 (FIG. 3), the sensor 122 with its tip 150 penetrates the septum 134 sealing the compartment 128. The compartment 128 can contain a further calibrating agent or a cleaning agent, so that the sensor 122 and its sensitive element 146 can be calibrated and cleaned in the desired way.

Figure 8:
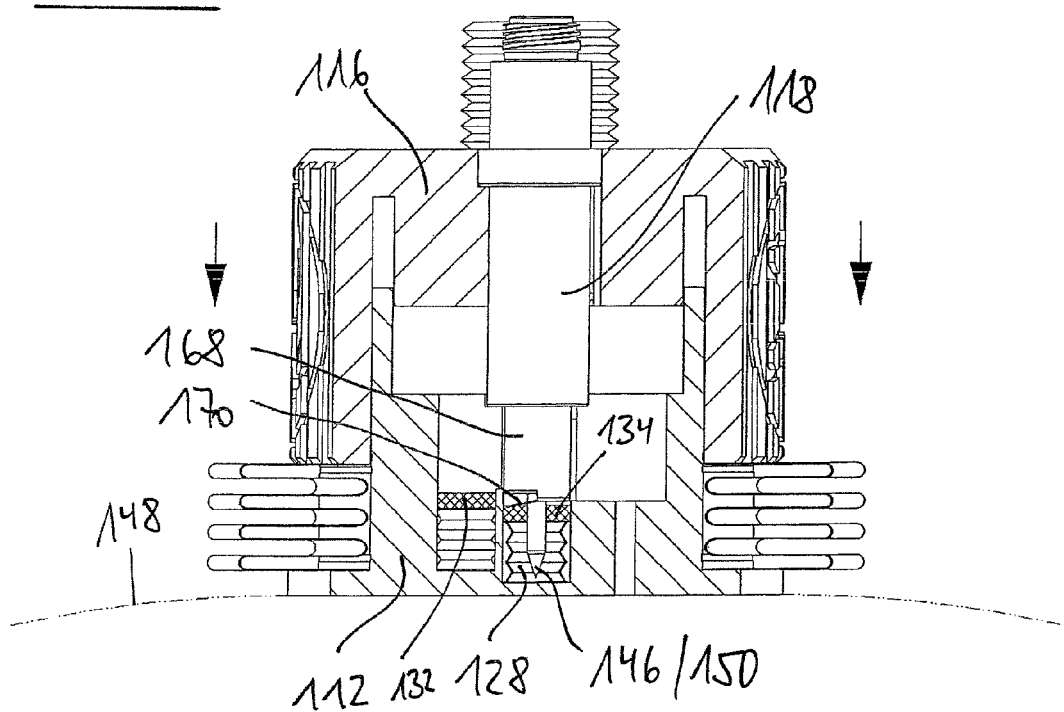
Figure 9:
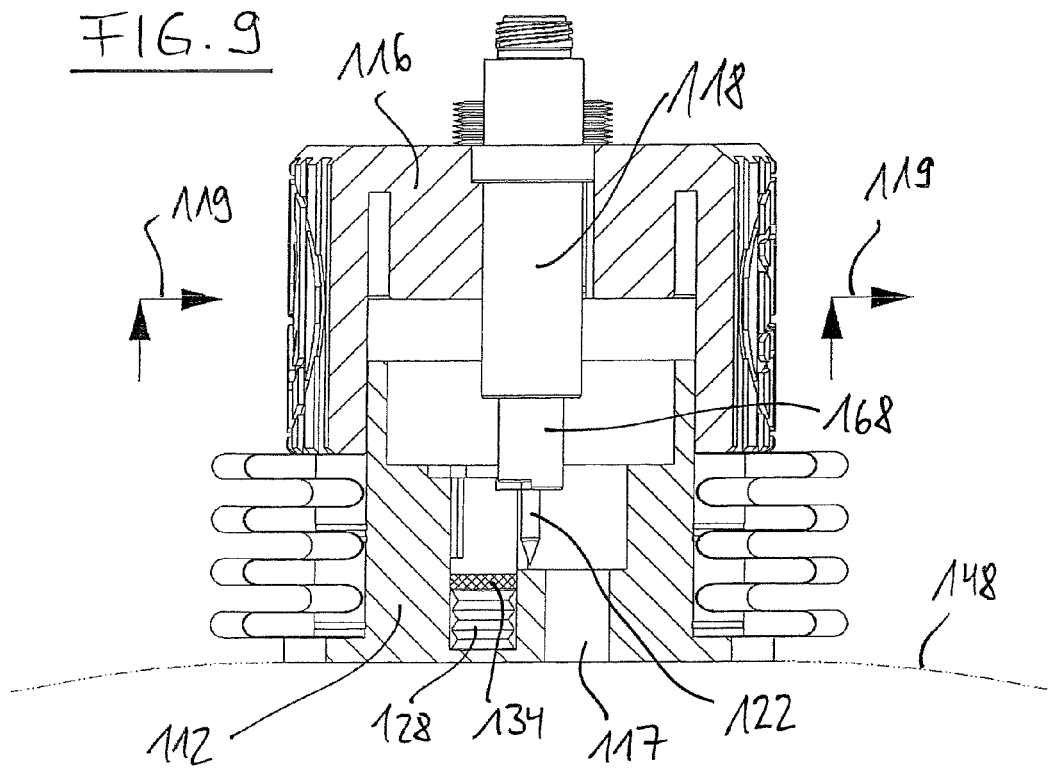
Figure 10:
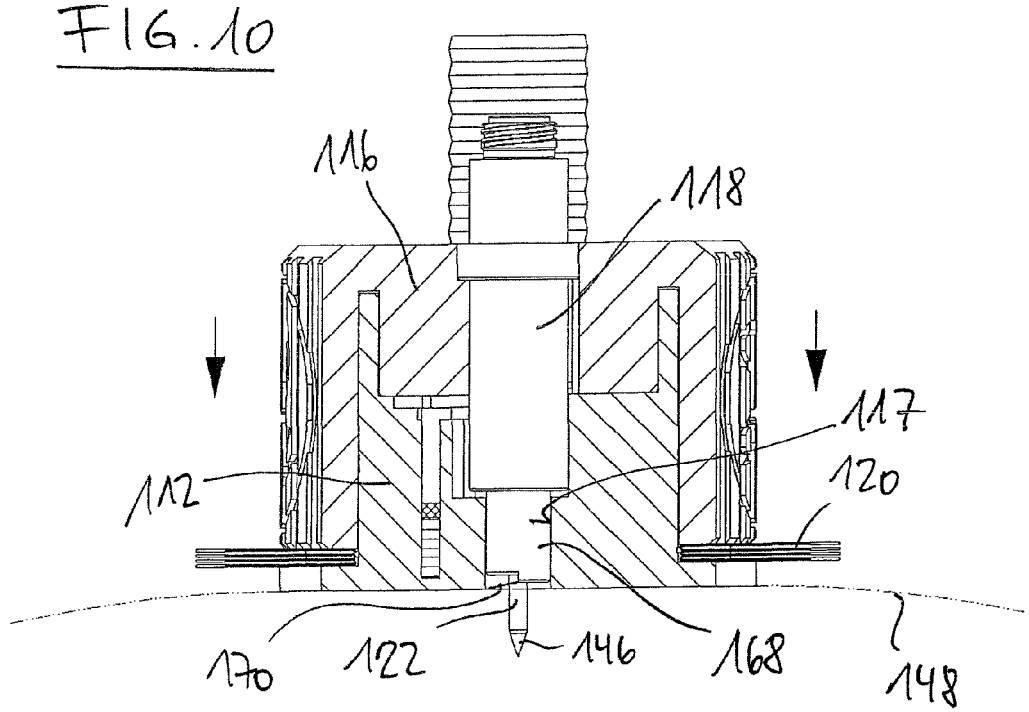

After the calibration and cleaning step illustrated in FIG. 8 has been carried out, the actuating element 116 can be moved again in the direction away from the fermenter and then turned further anti-clockwise until the sensor 122 is substantially in alignment with the passage opening 117. An intermediate position during the rotation can be seen in FIG. 9, and FIG. 10 shows the measurement readiness position, in which the actuating element is moved fully downwards through the opening 117 towards the fermenter 148, so that the sensor 122 and its sensitive element 146 are arranged in the interior (reaction space) of the fermenter 148 (reaction vessel).

As regards designing and executing the compartments 126, 128 with rigid or elastic walls, reference is made to the introductory comments.

It should also be noted that the septa or stripping elements have, in addition to their sealing function of the compartments and the cleaning function for the sensor, also a function that stabilises the sensor in its position in a respective compartment. By way of example reference is made once more to FIGS. 1 and 2, which show a supporting ring 72 arranged above the compartments 26, 28, 30, which can ensure a radial guidance of the relatively long sensor 122 in particular through the first two compartments 26 and 28.

Preliminary tests have already been carried out with a sensor unit 10 according to the first embodiment (FIGS. 1 and 2). In the test two compartments were filled with pH buffer gels of pH 4 and pH 7, and a pH single-rod measuring chain with a conical glass cone was used. The viscosities of the two calibrating gels were chosen to be relatively high (>5,000 mPa/s). The pH buffer gel of pH 4 served as storage gel. The septa of the compartments consisted of a double-layered LDPE film, which was screwed with a screw plug into a thread. After 30 days' storage the pH single-rod measuring chain was calibrated in an overhead position, not shown in the figures, in the two calibrating gels buffer gel pH 4 and buffer gel pH 7 according to the procedure described with reference to FIGS. 1 and 2. A pH check measurement was then carried out in a buffer gel of pH 4 arranged separated from the compartments outside the calibrating unit. A very good agreement between the theoretical values and the measured pH values was found in this case. In addition a very good cleaning of the pH electrodes (sensitive element 46) was achieved by the septa. No noticeable gel residues were found on the sensor nor any leakage of gel into the reaction space (fermenter).

The sensor units 10, 110 proposed here can be firmly connected, in particular screwed or bonded or welded, to a disposable fermenter. The calibrating units and in particular their calibrating agents and cleaning agents and sensors are implemented so that the fermenter together with the calibratable sensor units attached thereto can be reliably sterilised. Accordingly conventional and proven sensors in particular can be used with disposable fermenters without the fermenter being contaminated during the attachment and/or calibration of the sensors.

The invention claimed is:

1. A method for calibrating at least one sensor device of a sensor unit connected to a reaction vessel, wherein the sensor unit comprises at least one sensor device configured to be calibrated, at least one compartment containing a calibrating agent, and a housing, wherein the at least one sensor device and the at least one compartment are accommodated movably relative to one another in the housing which is configured to be connected to the reaction vessel, wherein the sensor unit is arranged so as to calibrate the at least one sensor device by contact with the calibrating agent before chemical and/or physical parameters of a measurement substance are measured with the at least one sensor device, wherein the at least one sensor device is further configured such that the relative movement between the at least one sensor device and the at least one compartment is irreversible, wherein the at least one sensor device is movable relative to the at least one compartment from an initial position in which the at least one sensor device does not contact the measurement substance into a measurement readiness position different from the initial position, in which the at least one sensor device is at least partially contactable by the measurement substance, wherein the method comprises the steps of:

inserting a sensitive element of the at least one sensor device into a compartment of the sensor unit containing a calibrating agent, withdrawing the sensitive element from the compartment;

inserting the sensitive element into the reaction vessel and locking the sensor device in position, wherein the steps of the method are irreversible.

2. The method according to claim 1, further comprising the steps of:

inserting the sensitive element of the at least one sensor device into at least one further compartment of the sensor unit containing a second calibrating agent or a cleaning agent, and withdrawing the sensitive element from the at least one further compartment;

wherein the steps of inserting the sensitive element of the at least one sensor device into at least one further compartment and withdrawing the sensitive element from the at least one further compartment are performed before inserting the sensitive element into the reaction vessel.

3. The method according to claim 2, wherein the at least one sensor device is guided such that the sensitive element does not come into contact with a preceding compartment.

4. The method according to claim 1, wherein the reaction vessel is a fermenter.

5. The method according to claim 1, wherein the reaction vessel is a disposable fermenter.

6. The method according to claim 3, wherein the at least one sensor device is temporary stopped so that the sensitive element does not come into contact with a preceding compartment.

* * * * *

UNITED STATES PATENT AND TRADEMARK OFFICE
CERTIFICATE OF CORRECTION

PATENT NO. : 9,034,572 B2
APPLICATION NO. : 13/930174
DATED : May 19, 2015
INVENTOR(S) : Andreas Loebbert et al.

Page 1 of 1

It is certified that error appears in the above-identified patent and that said Letters Patent is hereby corrected as shown below:

*On the Title Page*

Under item (62) Related U.S. Application Data,
"filed on Feb. 20, 2011" should read -- filed on Feb. 10, 2011 --.

Signed and Sealed this
Twenty-seventh Day of October, 2015

Michelle K. Lee
*Director of the United States Patent and Trademark Office*